US011246986B2

(12) United States Patent
Wilinska et al.

(10) Patent No.: US 11,246,986 B2
(45) Date of Patent: Feb. 15, 2022

(54) INTEGRATED CLOSED-LOOP MEDICATION DELIVERY WITH ERROR MODEL AND SAFETY CHECK

(71) Applicants: Abbott Diabetes Care Inc., Alameda, CA (US); Cambridge Enterprise Limited, Cambridge (GB)

(72) Inventors: Malgorzata E. Wilinska, Cambridge (GB); Erwin S. Budiman, Fremont, CA (US); Gary A. Hayter, Oakland, CA (US); Marc B. Taub, Mountain View, CA (US); Roman Hovorka, Cambridge (GB)

(73) Assignee: Abbott Diabetes Care Inc., Alameda, CA (US)

( * ) Notice: Subject to any disclaimer, the term of this patent is extended or adjusted under 35 U.S.C. 154(b) by 273 days.

(21) Appl. No.: 16/251,572

(22) Filed: Jan. 18, 2019

(65) Prior Publication Data
US 2019/0151540 A1      May 23, 2019

Related U.S. Application Data

(60) Continuation of application No. 15/193,804, filed on Jun. 27, 2016, now abandoned, which is a
(Continued)

(51) Int. Cl.
*A61M 5/172* (2006.01)
*A61B 5/1495* (2006.01)
(Continued)

(52) U.S. Cl.
CPC ......... *A61M 5/1723* (2013.01); *A61B 5/1495* (2013.01); *A61B 5/14532* (2013.01);
(Continued)

(58) Field of Classification Search
CPC ............. A61B 5/14532; A61B 5/1495; A61M 2005/14208; A61M 2005/14292;
(Continued)

(56) References Cited

U.S. PATENT DOCUMENTS 5,840,020 A    11/1998  Heinonen et al.
6,656,148 B2   12/2003  Das et al.
(Continued)

FOREIGN PATENT DOCUMENTS

WO     20005041103 A2      5/2005
WO     2007116226 A2     10/2007
WO     WO-2007116226 A2 * 10/2007 ......... A61B 5/14532

OTHER PUBLICATIONS

Hovorka, Roman et al.: "Nonlinear model predictive control of glucose concentration in subjects with type 1 diabetes; Controlling glucose" Physiological Measurement, Institute of Physics Publishing, Bristol, GB, vol. 25, No. 4, Aug. 1, 2004 (Aug. 1, 2004), pp. 905-920, XP020074167, ISSN: 0967-3334, p. 916, line 1-line 14.

*Primary Examiner* — Quynh-Nhu H. Vu
(74) *Attorney, Agent, or Firm* — Sterne, Kessler, Goldstein & Fox P.L.L.C.

(57) ABSTRACT

A closed-loop system for insulin infusion overnight uses a model predictive control algorithm ("MPC"). Used with the MPC is a glucose measurement error model which was derived from actual glucose sensor error data. That sensor error data included both a sensor artifacts component, including dropouts, and a persistent error component, including calibration error, all of which was obtained experimentally from living subjects. The MPC algorithm advised on insulin infusion every fifteen minutes. Sensor glucose input to the MPC was obtained by combining model-calculated, noise-free interstitial glucose with experimentally-derived transient and persistent sensor artifacts associated with the FreeStyle Navigator® Continuous Glucose
(Continued)

Monitor System ("FSN"). The incidence of severe and significant hypoglycemia reduced 2300- and 200-fold, respectively, during simulated overnight closed-loop control with the MPC algorithm using the glucose measurement error model suggesting that the continuous glucose monitoring technologies facilitate safe closed-loop insulin delivery.

20 Claims, 10 Drawing Sheets

Related U.S. Application Data continuation of application No. 14/083,336, filed on Nov. 18, 2013, now Pat. No. 9,402,953, which is a continuation of application No. 13/240,855, filed on Sep. 22, 2011, now Pat. No. 8,585,637, which is a division of application No. 12/751,668, filed on Mar. 31, 2010, now Pat. No. 8,062,249.

(60) Provisional application No. 61/248,353, filed on Oct. 2, 2009, provisional application No. 61/173,133, filed on Apr. 27, 2009, provisional application No. 61/165,467, filed on Mar. 31, 2009.

(51) Int. Cl.
*A61M 5/142* (2006.01)
*A61B 5/145* (2006.01)
*G16H 20/17* (2018.01)

(52) U.S. Cl.
CPC ............ *A61M 5/142* (2013.01); *G16H 20/17* (2018.01); *A61M 2005/14208* (2013.01); *A61M 2005/14292* (2013.01); *A61M 2005/14296* (2013.01); *A61M 2205/50* (2013.01); *A61M 2205/52* (2013.01); *A61M 2205/70* (2013.01); *A61M 2230/201* (2013.01)

(58) Field of Classification Search
CPC .... A61M 2005/14296; A61M 2205/50; A61M 2205/52; A61M 2205/70; A61M 2230/201; A61M 5/142; A61M 5/1723; G16H 20/17
See application file for complete search history.

(56) References Cited

U.S. PATENT DOCUMENTS

| | | | |
|---|---|---|---|
| 7,920,906 B2 | 4/2011 | Goode, Jr. et al. | |
| 8,062,249 B2 | 11/2011 | Wilinska et al. | |
| 8,527,208 B2 | 9/2013 | Prud'homme et al. | |
| 8,585,637 B2 | 11/2013 | Wilinska et al. | |
| 2004/0034295 A1* | 2/2004 | Salganicoff | A61B 5/14532 600/365 |
| 2006/0253296 A1 | 11/2006 | Liisberg et al. | |
| 2007/0173761 A1 | 7/2007 | Kanderian et al. | |
| 2008/0071158 A1 | 3/2008 | McGarraugh et al. | |
| 2008/0161664 A1 | 7/2008 | Mastrototaro et al. | |
| 2008/0172031 A1 | 7/2008 | Blomquist | |
| 2008/0183060 A1* | 7/2008 | Steil | A61B 5/6849 600/365 |
| 2008/0208113 A1* | 8/2008 | Damiano | A61M 5/1723 604/67 |
| 2014/0039383 A1 | 2/2014 | Dobbles et al. | |

* cited by examiner

INTEGRATED CLOSED-LOOP MEDICATION DELIVERY WITH ERROR MODEL AND SAFETY CHECK

CROSS-REFERENCE TO RELATED APPLICATIONS

The present application is a continuation of U.S. application Ser. No. 14/083,336 filed Nov. 18, 2013, which is a continuation of U.S. application Ser. No. 13/240,855 filed Sep. 22, 2011, now U.S. Pat. No. 8,585,637, which is a divisional of U.S. application Ser. No. 12/751,668 filed Mar. 31, 2010, now U.S. Pat. No. 8,062,249, which claims the benefit of U.S. Provisional Application No. 61/248,353, filed Oct. 2, 2009, U.S. Provisional Application No. 61/173,133, filed Apr. 27, 2009, and U.S. Provisional Application No. 61/165,467, filed Mar. 31, 2009, all of which are incorporated herein by reference in their entireties for all purposes.

BACKGROUND

The invention is generally directed to an integrated system of blood glucose level detection and use of that information in setting insulin delivery parameters, and more particularly, to the use of actual sensor data in characterizing a sensor for use in performing preclinical closed-loop trial studies in silico.

Diabetes is a metabolic disorder that afflicts tens of millions of people throughout the world. Diabetes results from the inability of the body to properly utilize and metabolize carbohydrates, particularly glucose. Normally, the finely-tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock.

In patients with insulin-dependent diabetes, the symptoms of the disease can be controlled by administering additional insulin (or other agents that have similar effects) by injection or by external or implantable insulin pumps. The "correct" insulin dosage is a function of the level of glucose in the blood. Ideally, insulin administration should be continuously readjusted in response to changes in blood glucose level. In diabetes management, "insulin" instructs the body's cells to take in glucose from the blood. "Glucagon" acts opposite to insulin, and causes the liver to release glucose into the blood stream. The "basal rate" is the rate of continuous supply of insulin provided by an insulin delivery device (pump). The "bolus" is the specific amount of insulin that is given to raise blood concentration of the insulin to an effective level when needed (as opposed to continuous).

Presently, systems are available for continuously monitoring blood glucose levels by implanting a glucose sensitive probe into the patient. Such probes measure various properties of blood or other tissues, including optical absorption, electrochemical potential, and enzymatic products. The output of such sensors can be communicated to a hand held device that is used to calculate an appropriate dosage of insulin to be delivered into the blood stream in view of several factors, such as a patient's present glucose level, insulin usage rate, carbohydrates consumed or to be consumed, and exercise, among others. These calculations can then be used to control a pump that delivers the insulin, either at a controlled basal rate, or as a bolus. When provided as an integrated system, the continuous glucose monitor, controller, and pump work together to provide continuous glucose monitoring and insulin pump control.

Such systems at present require intervention by a patient to calculate and control the amount of insulin to be delivered. However, there may be periods when the patient is not able to adjust insulin delivery. For example, when the patient is sleeping, he or she cannot intervene in the delivery of insulin, yet control of a patient's glucose level is still necessary. A system capable of integrating and automating the functions of glucose monitoring and controlled insulin delivery would be useful in assisting patients in maintaining their glucose levels, especially during periods of the day when they are unable to intervene.

Since the year 2000, at least five continuous or semi-continuous glucose monitors have received regulatory approval.[1] In combination with continuous subcutaneous insulin infusion ("CSII"),[2] these devices have promoted research toward closed-loop systems, which deliver insulin according to real-time needs, as opposed to open-loop systems which lack the real-time responsiveness to changing glucose levels. A closed-loop system, also called the "artificial pancreas," consists of three components: a glucose monitoring device such as a continuous glucose monitor ("CGM") that measures subcutaneous glucose concentration ("SC"); a titrating algorithm to compute the amount of analyte such as insulin and/or glucagon to be delivered; and one or more analyte pumps to deliver computed analyte doses subcutaneously. So far, only a few prototypes have been developed, and testing has been confined to clinical settings.[3-8] However, an aggressive concerted effort promises accelerated progress toward home testing of closed-loop systems.

The development, evaluation, and testing of closed-loop systems are time-consuming, costly, and confounded by ethical and regulatory issues. Apart from early stage testing in animals such as the dog[9,10] or the swine,[11] testing in the computer (virtual) environment, also termed in silico testing, is the only other alternative to evaluate and optimize control algorithms outside human studies. Chassin and colleagues have developed a simulation environment and testing methodology[12] using a glucoregulatory model developed in a multitracer study[13] and evaluated a glucose controller developed within the Adicol Project.[14] Another simulator has been reported by Cobelli and associates,[15] building on model-independent quantification of glucose fluxes occurring during a meal.[16] The latter simulator has been accepted by the U.S. Food and Drug Administration to replace animal testing. Patek and coworkers provided guidelines for preclinical testing of control algorithms.[17]

However, such simulations have used mathematical models of glucose sensors in which random data is used for simulating errors of the sensor. Random number generators are used to simulate random errors of such sensors based on noise of the sensor. Such data are therefore not based on the actual performance of any particular sensor and are likely to have a significant level of inaccuracy.

Closed-loop systems may revolutionize management of type 1 diabetes mellitus ("T1DM"), but their introduction is likely to be gradual, starting from simpler applications such as hypoglycemia prevention or overnight glucose control and progressing to more complex approaches such as twenty-four hours per day/seven days per week (24/7) glucose control.[8] The main reason for gradual deployment is the uncertain risk of hypoglycemia and hyperglycemia, which may arise due to (1) intrinsic overdosing and underdosing of insulin by a control algorithm, and (2) persistent and transient differences between plasma glucose ("PG") and sensor glucose ("SG"). The transient differences could be either of physiological origin (SC glucose kinetics) or due to a temporal CGM device artifact. The persistent differences result from the CGM calibration error ("CE"). The relatively slow absorption of subcutaneously administered "rapid-acting" insulin analogues and other system imperfections such as pump delivery errors may exacerbate the hypoglycemia and hyperglycemia risks.

Hence, those of skill in the art have recognized a need for an integrated, automated system combining continuous glucose monitoring and controlled insulin delivery. Such a system would include various features to insure the accuracy of the glucose monitor and to protect the user from either under- or over-dosage of insulin. The system would include various functions for improving the accuracy, usability, control, and safety of the system, including a variety of alarms which could be set by a user or a technician to avoid false alarms while ensuring adequate sensitivity to protect the user. Those skilled in the art have also recognized a need for a more accurate glucose measurement error model for increasing the accuracy of closed-loop systems. The present invention fulfills these, and other needs.

SUMMARY OF THE INVENTION

Briefly and in general terms, the present invention is directed to a system for the delivery of insulin to a patient, the system comprising a glucose sensor configured to provide a sensor glucose measurement signal representative of sensed glucose, an insulin delivery device configured to deliver insulin to a patient in response to control signals, and a controller programmed to receive the sensor glucose measurement signal and to provide a delivery control signal to the delivery device as a function of the received sensor glucose measurement signal in accordance with a control model and a glucose measurement error model, wherein the glucose measurement error model is derived from actual glucose sensor measurement data.

In more detailed aspects, the glucose measurement error model is derived solely from actual glucose sensor measurement data. In another aspect, the glucose measurement error model is derived solely from actual glucose sensor error data, excluding sensor noise data. In another aspect, the glucose measurement error model is derived solely from actual glucose sensor measurement data to the exclusion of randomly-generated variable data. In yet a further aspect, the glucose measurement error model is derived solely from a fixed time history of error data from actual use of a glucose sensor of the same type as the sensor of the system. And in yet another aspect, the glucose measurement error model is derived from actual glucose sensor measurement data from a glucose sensor of the same type as the sensor of the system.

In more detailed aspects, the control model comprises a model predictive control and the controller is also programmed to provide the delivery control signals to the delivery device as a function of a model predictive control. The glucose measurement error model is derived from calibration error of the glucose sensor, which comprises the difference between a plasma glucose level and the sensor glucose level signal of the glucose sensor. Further, the glucose measurement error model is derived from a glucose sensor dropout reading.

In other aspects, the controller is further programmed to recalibrate the system when the difference between the received sensor glucose level signal and a plasma glucose level exceeds a predetermined level. The delivery control signal is also a function of the weight of a patient, a total daily insulin dose, and a basal insulin profile, and wherein the controller is also programmed to calculate from the control model an accepted value, the controller is also programmed to calculate from the glucose level signal an inferred value, the controller is also programmed to forecast a future plasma glucose level excursion based on the accepted value and inferred value, and the controller is also programmed to adjust the delivery control signal in accordance with the forecast future plasma glucose level excursion. In more detailed aspects, the accepted value comprises an insulin sensitivity of the patient, a glucose distribution volume, and an insulin distribution volume, and the inferred value comprises glucose flux and a carbohydrate bioavailability.

In yet further aspects, the controller is also programmed to adjust a value of the delivery control signal in accordance with a safety check. Such safety check comprises at least one of imposing a maximum infusion rate related to a basal rate depending on a current sensor glucose level, time since a previous meal, and carbohydrate content of a meal, shutting off insulin delivery at a predetermined low sensor glucose value, reducing insulin delivery when sensor glucose is decreasing rapidly, and capping the insulin infusion to a pre-programmed basal rate if an insulin delivery pump occlusion is inferred.

In another aspect, the glucose sensor, the insulin delivery device, and the controller are virtual devices, each being programmed for in silico testing of a system for delivery of insulin to a virtual patient.

The invention is also directed to a method for delivering insulin to a patient, the method comprising sensing a glucose level and providing a glucose measurement signal representative of the sensed glucose, providing a control signal as a function of the glucose measurement signal in accordance with a control model and a glucose measurement error model, wherein the glucose measurement error model is derived from actual/experimental glucose sensor data, and delivering insulin in response to the control signal. In a more detailed aspect, providing the control signal further comprises producing the control signal in accordance with a model predictive control.

In more detailed aspects, the glucose measurement error model used in the method is derived solely from actual glucose sensor measurement data. In another aspect, the glucose measurement error model is derived solely from actual glucose sensor error data, excluding sensor noise data. In another aspect, the glucose measurement error model is derived solely from actual glucose sensor measurement data to the exclusion of randomly-generated variable data. In yet a further aspect, the glucose measurement error model is derived solely from a fixed time history of error data from actual use of a glucose sensor of the same type as the sensor of the system. And in yet another aspect, the glucose measurement error model is derived from actual glucose sensor measurement data from a glucose sensor of the same type as the sensor of the system.

Further, more detailed aspects include determining a calibration error of a glucose sensor from actual sensor data, based on the difference between a plasma glucose level and the glucose level signal and deriving the glucose measurement error model therefrom. Deriving the glucose measurement error model further comprises determining a glucose sensor dropout reading from actual sensor data and deriving the glucose measurement error model therefrom.

Other aspects include providing the control signal as a function of the weight of a patient, a total daily insulin dose, and a basal insulin profile, the method further comprising determining, based on the control model, at least one accepted value, calculating from the glucose level signal at least one inferred value, adjusting the control model in accordance with the accepted value and inferred value, and forecasting a future plasma glucose level excursion based on the control model. Determining the accepted value comprises basing the determination on an insulin sensitivity of the patient, a glucose distribution volume, and an insulin distribution volume. Calculating the inferred value comprises calculating the inferred value also from glucose flux and a carbohydrate bioavailability.

In yet further aspects, the method further comprises adjusting a value of the control signal in accordance with a safety check, comprising at least one of imposing a maximum infusion rate related to a basal rate depending on a current sensor glucose level, time since a previous meal, and carbohydrate content of a meal, shutting off insulin delivery at a sensor glucose of 77 mg/dl, reducing insulin delivery when sensor glucose is decreasing rapidly, and capping the insulin infusion to a pre-programmed basal rate if an insulin delivery pump occlusion is inferred.

In another aspect, the sensing, providing a control signal, and delivering insulin are performed virtually, each occurring for in silico testing of a method for delivery of insulin to a virtual patient.

The features and advantages of the invention will be more readily understood from the following detailed description that should be read in conjunction with the accompanying drawings.

DETAILED DESCRIPTION OF THE PREFERRED EMBODIMENTS

Figure 1A:
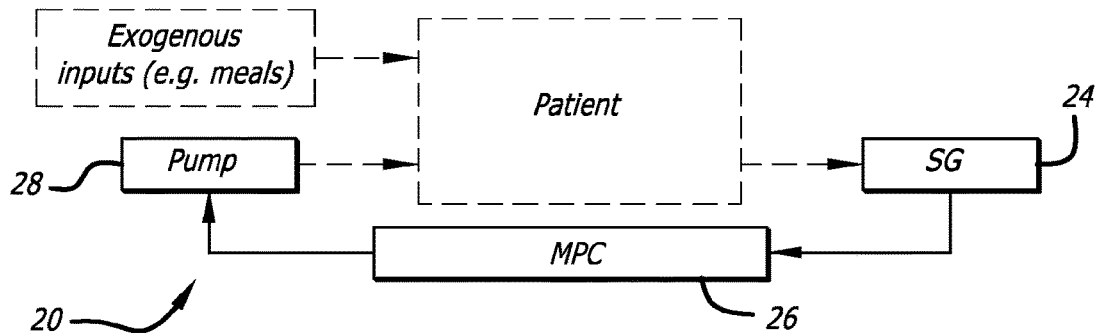
FIG. 1A presents a block diagram of a closed-loop insulin infusion system using a model predictive controller.

Referring now in more detail to the exemplary drawings for purposes of illustrating embodiments of the invention, wherein like reference numerals designate corresponding or like elements among the several views, there is shown in FIG. 1A a basic block diagram of a closed-loop system 20 for continuous glucose monitoring and for continuous subcutaneous insulin infusion using a model predictive controller 26. The patient receives exogenous inputs, such as meals. The patient's glucose is measured 24, evaluated by the model predictive controller (MPC) and is used by the MPC to control a delivery device, such as a pump 28, to deliver medication to the patient to control blood glucose.

Glucose Control Algorithm

Figure 1B:
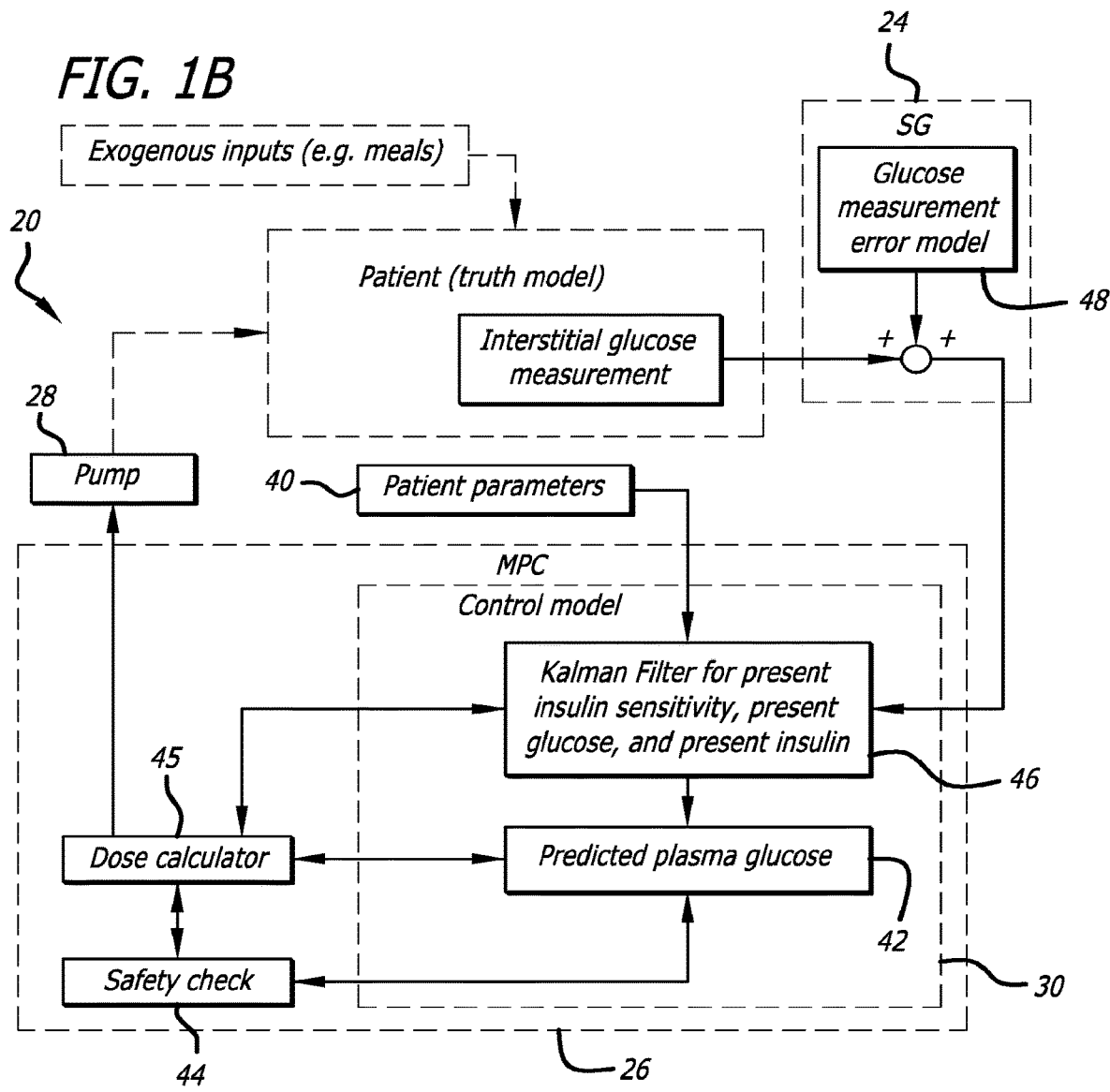
FIG. 1B presents a block diagram of a closed-loop insulin infusion system using a glucose measurement error model in accordance with aspects of the invention.

Referring now to FIG. 1B, a control algorithm was used based on the model predictive control ("MPC") paradigm[18] to deliver insulin in a closed-loop fashion. Interstitial glucose measurement occurs and every fifteen minutes, simulated real-time sensor glucose ("SG") 24 was fed into the MPC controller 26, which calculated subcutaneous glucose concentration ("SC") insulin infusion for the insulin pump 28. A dose calculator 45 is included in this embodiment. The MPC controller 26 adopts a compartment model of glucose kinetics describing the effect of (1) SC rapid-acting insulin analogue and (2) the carbohydrate ("CHO") content of meals on SG excursions. A list of abbreviations used in the specification and drawings and the items they stand for is included at the end of the specification.

The glucoregulatory model is initialized using a subject's weight, total daily insulin dose, and the basal insulin profile (patient parameters) 40. These values feed into estimates of temporal insulin sensitivity and glucose and insulin distribution volumes. Using a Kalman filter 46 approach, real-time SG measurements are used to update two model parameters: (1) a glucose flux quantifying model misspecification; and (2) CHO bioavailability. Several competing models differing in the rate of SC insulin absorption and action and the CHO absorption profile are run in parallel. A computationally efficient, stochastic-based approach is used to derive a combined control model 30 that best explains observed SG excursions.[19]

Following estimation of model parameters, the combined control model 30 is used to forecast plasma glucose ("PG")

42 excursions over a two and one-half hour prediction horizon. A sequence of standard deviation ("SD") insulin infusion rates is determined, which approximates the desired PG trajectory, characterized by a slow decline from hyperglycemia and a rapid recovery from hypoglycemia to target glucose, which is set at minimum to 104 mg/dl but is elevated up to 132 mg/dl to take into account inaccuracies of model-based predictions. The first infusion rate from the sequence of SC insulin infusion rates is delivered by the insulin pump 28 subject to safety checks 44, which can reduce the infusion rate to prevent insulin overdosing. These checks include: (1) imposing a maximum infusion rate of two to five times the preprogrammed basal rate, depending on the current SG level, the time since the previous meal(s), and CHO content of meal(s); (2) shutting off insulin delivery at a SG of 77 mg/dl; (3) reducing insulin delivery when SG is decreasing rapidly; and (iv) capping the insulin infusion to the preprogrammed basal rate if a pump occlusion is inferred by the MPC 26.[22]

For the purposes of the present study, MPC algorithm Version 0.02.02 was used. Earlier versions of the algorithm were used in clinical studies for overnight closed-loop insulin delivery in children and adolescents with T1DM.[20-22]

Simulation Environment

A simulation environment designed to support the development of closed-loop insulin delivery systems was used.[12] The simulation environment is flexible and allows the following components to be defined: a model of glucose regulation, an experimental protocol, a glucose sensing model, an insulin pump model, and outcome metrics. A model of glucose kinetics and insulin action described by Hovorka and colleagues[14,23] was adopted. Other submodels include the model of SC insulin kinetics, the model of gut absorption, and the model of interstitial glucose (IG) kinetics.[23,24]

The simulator includes eighteen synthetic subjects (virtual patients) with T1DM defined by eighteen parameter sets, representing the virtual T1DM population. A subset of parameters were estimated from experimental data collected in subjects with T1DM,[14] and the remaining parameters were drawn from informed probability distributions.[13,23] The inter-subject variability is addressed through assigning a unique set of parameter values to each individual synthetic subject. The subjects vary, for instance, in their insulin sensitivity to glucose distribution, disposal, and endogenous glucose production.[14,23] The virtual subjects are characterized by their daily insulin requirements (0.35±0.14 U/day/kg), insulin-to-CHO ratio (1.7±1.0 U/10 g CHO), and body weight (74.9±14.4 kg). Intra-individual variability of the gluco-regulatory system is represented by superimposing oscillations on selected model parameters or adding random inter-occasion variability to parameter values. Sinusoidal oscillations with an amplitude of 5% and a three-hour period were superimposed on nominal values of most model parameters. Each parameter had a different phase generated randomly from a uniform distribution U [0.3 h]. Bioavailability of ingested CHO is characterized by 20% inter-occasion variability.

For the purposes of the present study, the glucose measurement error model 48 was derived from experimental data. The SG concentration was obtained as $SG(t)=IG(t)\times(1+CE)+D(t)$ where $IG(t)$ is noise-free interstitial glucose ("IG") concentration calculated by the glucoregulatory model and normalized such that, at the steady-state, it is identical to PG; CE is FreeStyle Navigator® Continuous Glucose Monitor System ("FSN") calibration error ("CE"), and $D(t)$ is the dropout trace of the FSN. The pump 28 delivery error model was assumed zero mean, uncorrelated, with a constant 5% coefficient of variation for the continuous insulin infusion and the insulin bolus. The simulation environment is implemented in Matlab® (The Mathworks, Natick, Mass.).

FreeStyle Navigator CGM System—Dropouts

The FreeStyle Navigator® Continuous Glucose Monitor system with TRUstart algorithm (Abbott Diabetes Care, Alameda, Calif.) was used for the present study. The FSN system occasionally exhibits a nonzero-mean signal artifact referred to here as "dropout," where certain mechanical perturbation of the sensor results in a momentarily attenuated glucose concentration.[25]

Dropouts were quantified using data from a study where fifty-eight living subjects with T1DM had simultaneously worn two sensors over the course of up to five days.[26] Values from the two sensors worn simultaneously on each subject were paired every minute. The point-wise difference between the paired glucose readings was computed. To account for residual CE, a segment's point-wise difference was normalized by subtracting the median bias of the segment.

From each pair, only time segments that overlap the night-time period were used, resulting in 285 night time segments. Segments with insufficient data, either due to a sensor starting or sending in the middle of the night time session or due to missing data, were excluded. In total, ninety-one segments were excluded because they contained less than 840 one-minute data points over the 900 minutes night-time session span. As a result, 194 night-time segments were available for simulation purposes.

The mean absolute difference in each segment was used to quantify dropout severity, and the 194 night-time sessions were separated into four quartiles. Ten dropout segments were chosen randomly from each quartile and used in simulation studies. The simulation environment adds the selected dropout segment onto the modeled IG concentration. Simulated CGM traces incorporating dropout data from each quartile are shown in FIG. 2.

Figure 2:
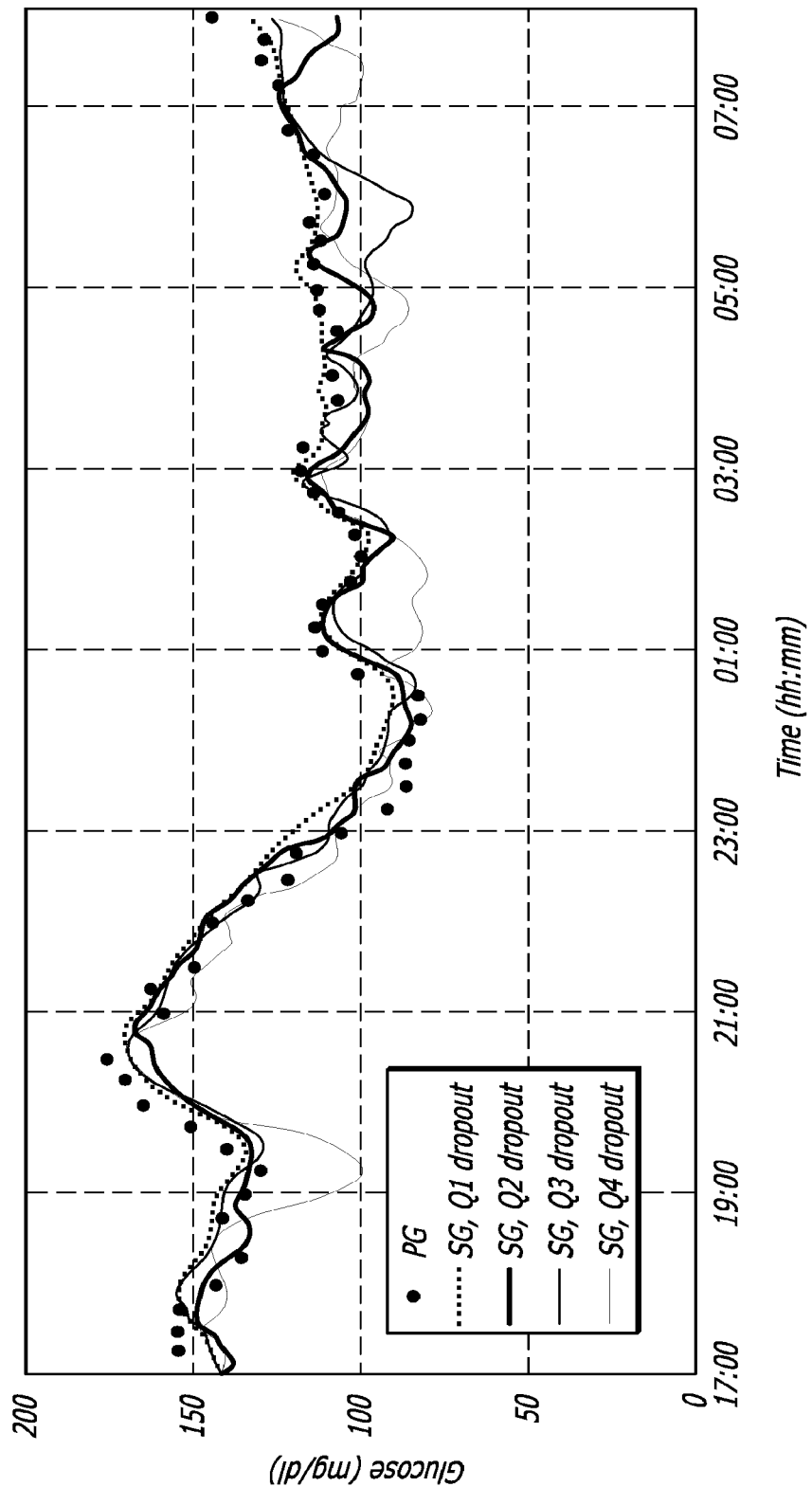
FIG. 2 shows simulated sensor glucose traces from the four quartiles of dropout severity alongside the underlying plasma glucose trace. Q1 represents negligible dropouts while Q4 represents the most severe dropouts.

FIG. 2 presents simulated sensor glucose traces from the four quartiles of dropout severity alongside the underlying plasma glucose trace. The first quartile Q1 represents negligible dropouts while the fourth quartile Q4 represents the most severe dropouts.

FreeStyle Navigator CGM System—Calibration Error

The FreeStyle Navigator System calibration error ("CE") is defined as CE=(SG–IG)/IG. In these simulations, therefore, a +5% CE means that the reported SG value is consistently 1.05 times higher than expected for a given IG concentration.

The FSN System is designed for five-day wear, with calibrations nominally scheduled at 1, 2, 10, 24, and 72 hours after sensor insertion. For the present study, a morning CGM sensor insertion is assumed for the night-time only closed-loop control. Thus, each night time, closed-loop session is assumed not to include a scheduled calibration, allowing CE to remain constant for the duration of the night session.

One-hundred and sixteen (116) insertions used to generate dropout signals in addition to 469 insertions from other studies with living subjects were used to generate a distribution of the FSN CE. The sensor data set comprised 248 living subjects with T1DM or type 2 diabetes mellitus ("T2DM") and were a combination of general sensor wear and in-clinic wear that included periods of specific glucose and insulin challenges.

As IG and PG are assumed to be identical at the steady state, CE can be approximated using an alternative definition: CE=(SG−PG)/PG. The CE for a single calibration session was calculated from pairs of SG-reference glucose values where all the SG values were derived from a single calibration and reference glucose used for calibration were excluded from the calculations. Unlike the calculation of dropouts, only reference glucose values measured from finger sticks using the inbuilt blood glucose meter were used. In addition, the real-time calibration of SG values used the FSN system with TRUstart algorithm.

Excluding calibration sessions containing less than ten SG-reference glucose pairs, 585 insertions yielded 1421 calibration sessions. The CE for each session was computed by comparing the median value of the relative difference between SG and reference glucose, and 1421 FSN CEs were generated using 35,200 SG-reference glucose pairs, yielding an average of 25 pairs for every calibration session.

Protocol of Simulation Studies

Figure 3:
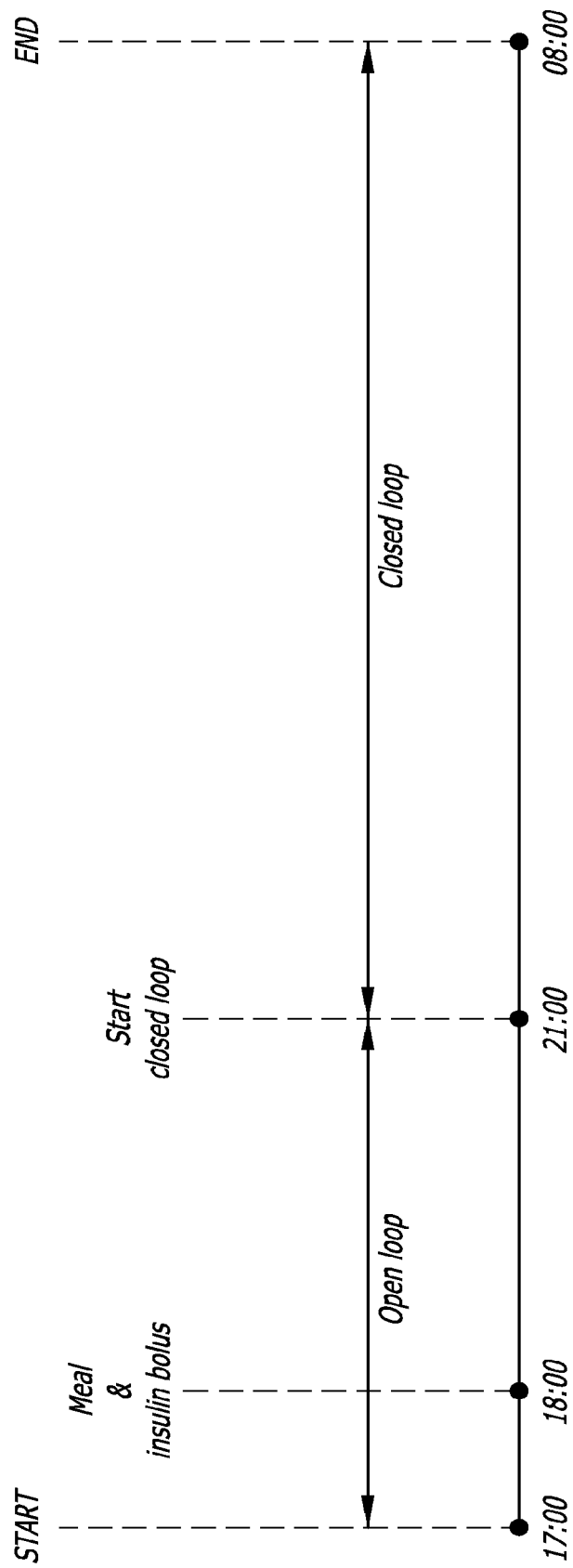
FIG. 3 provides a protocol of a simulated overnight closed-loop study showing a simulated study of fifteen hours duration, starting at 17:00 and ending at 08:00 the next day.

As shown in FIG. 3, the simulated study was fifteen hours long, starting at 17:00 and ending at 08:00 the next day. Plasma glucose at the start of the simulated study was drawn from a log-normal distribution, with a mean of 126 mg/dl constrained to a range from 72 to 180 mg/dl. A meal consisting of 50 g CHO was planned at 18:00 and was accompanied by a prandial insulin bolus. The insulin infusion rate between 17:00 and 21:00 was calculated using the simulation model of a particular virtual subject assuming steady-state conditions at the start of the experiment. At 21:00, the closed-loop glucose control algorithm took over the insulin delivery. The insulin infusion rate was calculated every fifteen minutes on the basis of CGM values, which included the dropout and CE components. Closed-loop control continued until the end of the simulated experiment at 08:00. Rescue CHOs (15 g CHO) were administered at SG values 63 mg/dl (3.5 mmol/liter) or below when confirmed by a PG value of 63 mg/dl or below, simulating a confirmatory finger stick glucose measurement. Correction insulin boluses were not administered at hyperglycemia.

The simulation studies were run in batches differing by the level of FSN CE. In total, 25 levels of FSN CEs ranging from −80% to +100% were simulated. The range covering 0% to 60% error was subdivided into 5% steps. The remaining range was spaced 10% apart. Each of the eighteen virtual subjects with T1DM was associated with one of forty randomly selected CGM dropout traces (ten traces from each of the four quartiles of increasing severity). This resulted in 720 different combinations and formed a single simulation batch. Each batch was run with all 25 levels of FSN CE, totaling 18,000 simulated overnight studies.

Open Loop Studies

Within the Artificial Pancreas Project at Cambridge ("APCam"), seventeen children and adolescents with T1DM treated by CSII for at least three months participated in the APCam01 study (monitoring study) and APCam03 (exercise study) conducted at the Wellcome Trust Clinical Research Centre, Addenbrooke's Hospital, University of Cambridge, UK. Informed consent was obtained from all study participants or their caregivers. The APCam01[20] and APCam03[22] clinical studies were originally designed to compare overnight closed-loop control against the standard CSII treatment. In the present analysis, only results from the CSII investigations are reported. The study protocols were approved by the Cambridgeshire 3 Ethics Committee. The subjects' demographic data are shown in TABLE 1. Four subjects participated in both studies.

In APCam01, on subject's arrival at the Clinical Research Facility at 16:00, a sampling cannula was inserted in a vein of an arm and kept patent with sodium chloride. At 18:00, the subjects ate a self-selected meal (87±23 g CHO) accompanied by prandial insulin (9±5 U; 31%±9% of total daily bolus amount) calculated according to the individual insulin-to-CHO ratio and supplemented by correction dose. Plasma glucose was determined every fifteen minutes from 17:00 to 08:00 the next day. At least two weeks before the first study, the CSII treatment was optimized by a healthcare professional by retrospectively analyzing seventy-two hours of nonreal-time SG data.

In APCam03, at least one week before the study, the subjects attended the Clinical Research Facility and a ramped treadmill protocol was used for the estimation of the peak $VO_2$ as an indicator of the maximum exercise effort. As used herein "$VO_2$" refers to the maximal oxygen uptake, which is widely accepted as a measure of cardiovascular fitness and maximal aerobic power. Continuous recording of $VO_2$ with breath-by-breath sampling was taken during the treadmill test and for two minutes during recovery after exercise test termination. Heart rate monitoring was maintained. On the study day, the subjects arrived at 15:00 at the Clinical Research Facility. A sampling cannula was inserted and kept patent with sodium chloride. At 16:00, subjects had a light meal chosen from a list of standardized snacks (45±13 g CHO, 12±3 g fat, 14±4 g protein) accompanied by prandial bolus (4±2 U). The subject exercised at 55% $VO_2$ max on the treadmill from 18:00 until 18:45, with a rest from 18:20 to 18:25. During exercise, basal insulin was left unmodified or was reduced according to individual guidelines. During the night, the subject's standard insulin pump settings were applied. Plasma glucose was determined every 15 min from 16:00 to 08:00 the next day. If PG dropped below 36 mg/dl, GlucoGel© (BBI Healthcare, UK) was given and the study night terminated.

Data Analysis

Severe and significant hypoglycemia was declared at PG≤36 mg/dl (2.0 mmol/liter) and ≤45 mg/dl (2.5 mmol/liter), respectively. These are levels when cognitive behavioral defenses are compromised.[27] Significant hyperglycemia was declared at PG≥300 mg/dl (16.7 mmol/liter).

The empirical probability distribution function of FSN CE was calculated from the 1421 calibration sessions discussed above. During simulated closed-loop studies, occurrence and duration of hypoglycemia and hyperglycemia based on the simulated PG trace were recorded from 21:00 to 008:00. The probability of hypoglycemia and hyperglycemia events occurring overnight at a given FSN CE is obtained as a product of the probability, $c_i$, of the given FSN CE and the probability of overnight hypoglycemia and hyperglycemia, $h_i$, at the given FSN CE. The overall event probability P is obtained as the sum of these products over the 25 levels of FSN CE, i.e., $P=\Sigma c_i h_i$. For APCam01 and APCam03 studies, the overall event probability is obtained as the number of hypoglycemia and hyperglycemia events divided by the number of overnight stays. The overall incidence is obtained as reciprocal to the overall event probability.

During simulated closed-loop studies, mean PG, mean SG, and time-in-target 80-145 mg/dl were calculated between 20:00 and 08:00 to assess the performance of the MPC algorithm at different levels of FSN CE. Values are shown as mean±standard deviation unless stated otherwise.

Simulated Closed-Loop Studies

Figure 4:
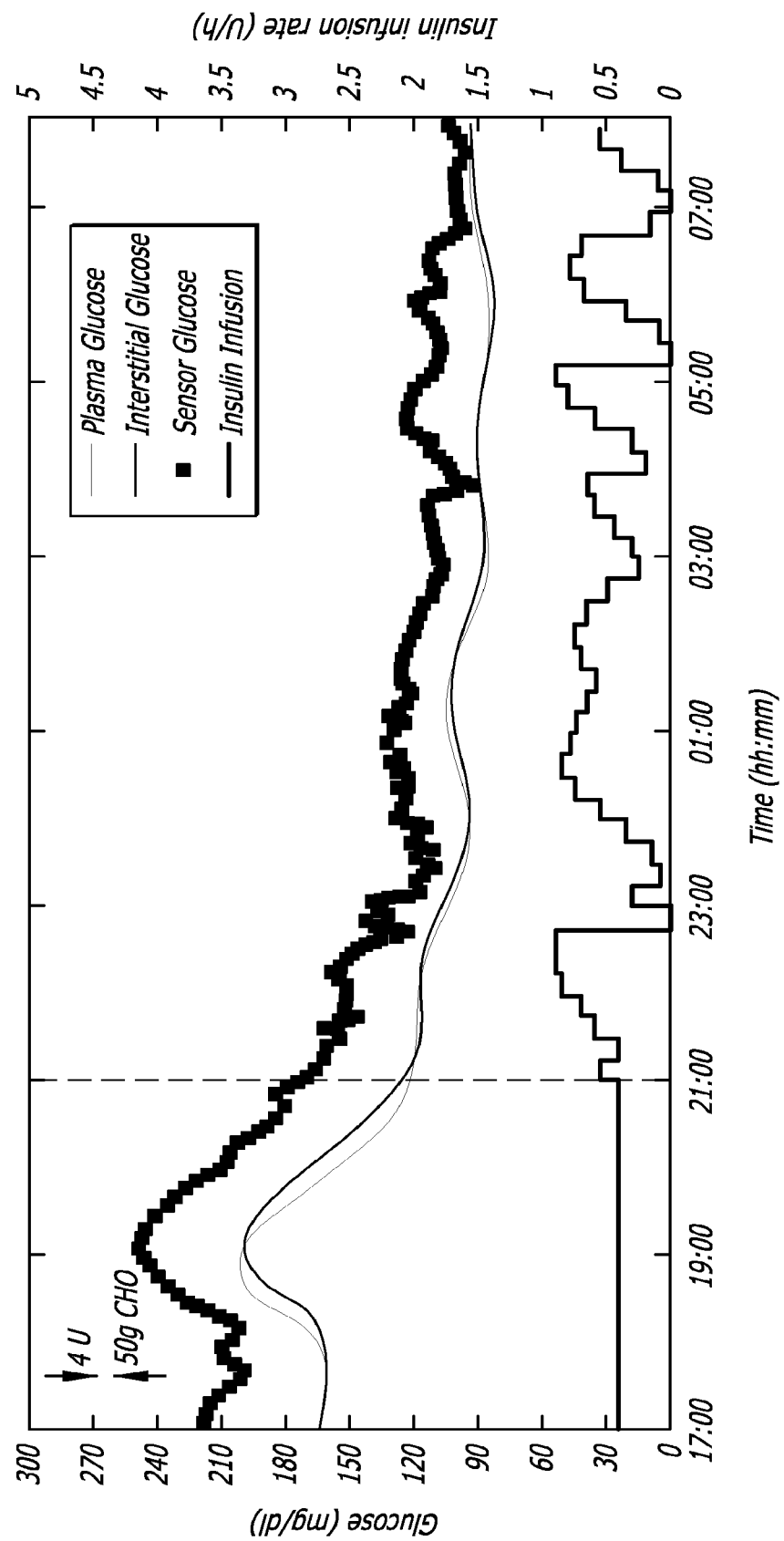
FIG. 4 shows a sample simulation of overnight closed-loop control adopting a +20% CGM system calibration error and a dropout trace from quartile two. The graph presents plasma glucose, interstitial glucose, sensor glucose, and insulin infusion.

A sample simulation study with +20% FSN CE using dropout trace from quartile two is shown in FIG. 4. Overall, 18,000 simulation studies were performed; 720 simulation studies were run for each of the 25 levels of FSN CE. During simulations, the MPC algorithm was unaware of FSN CE and the extent of the CGM dropout.

Figure 5:
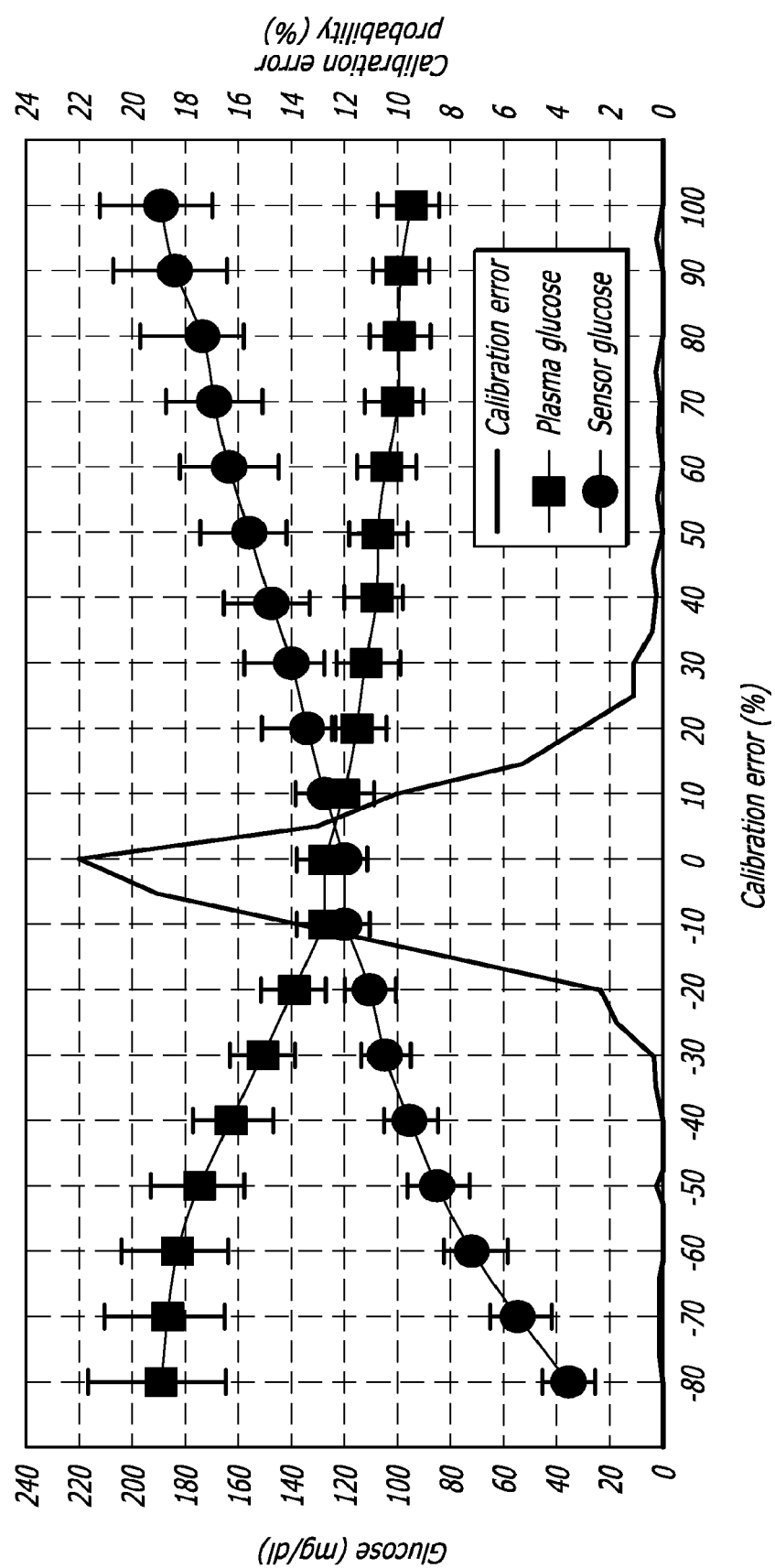
FIG. 5 is a graph showing plasma glucose and sensor glucose (median [interquartile range]; N=720 at each level) during simulated overnight closed-loop studies at different levels of CGM system calibration errors, The CGM system calibration error probability distribution function is also shown.

FIG. 5 shows PG and SG values obtained simultaneously during simulation studies at FSN CEs ranging from −80% to +100%. As expected, increasing levels of FSN CE result in progressively lower median PG. The MPC algorithm steps up insulin delivery to limit the increase in SG, unaware of progressively increasing gap between sensor and PG. Employing the SG values, the MPC algorithm performs less efficiently at high FSN CE (see FIG. 6, which plots time-in-target values.) However, employing the PG values, the MPC algorithm achieves 60% or higher time-in-target for FSN CE ranging from −20% to +100%.

Figure 7:
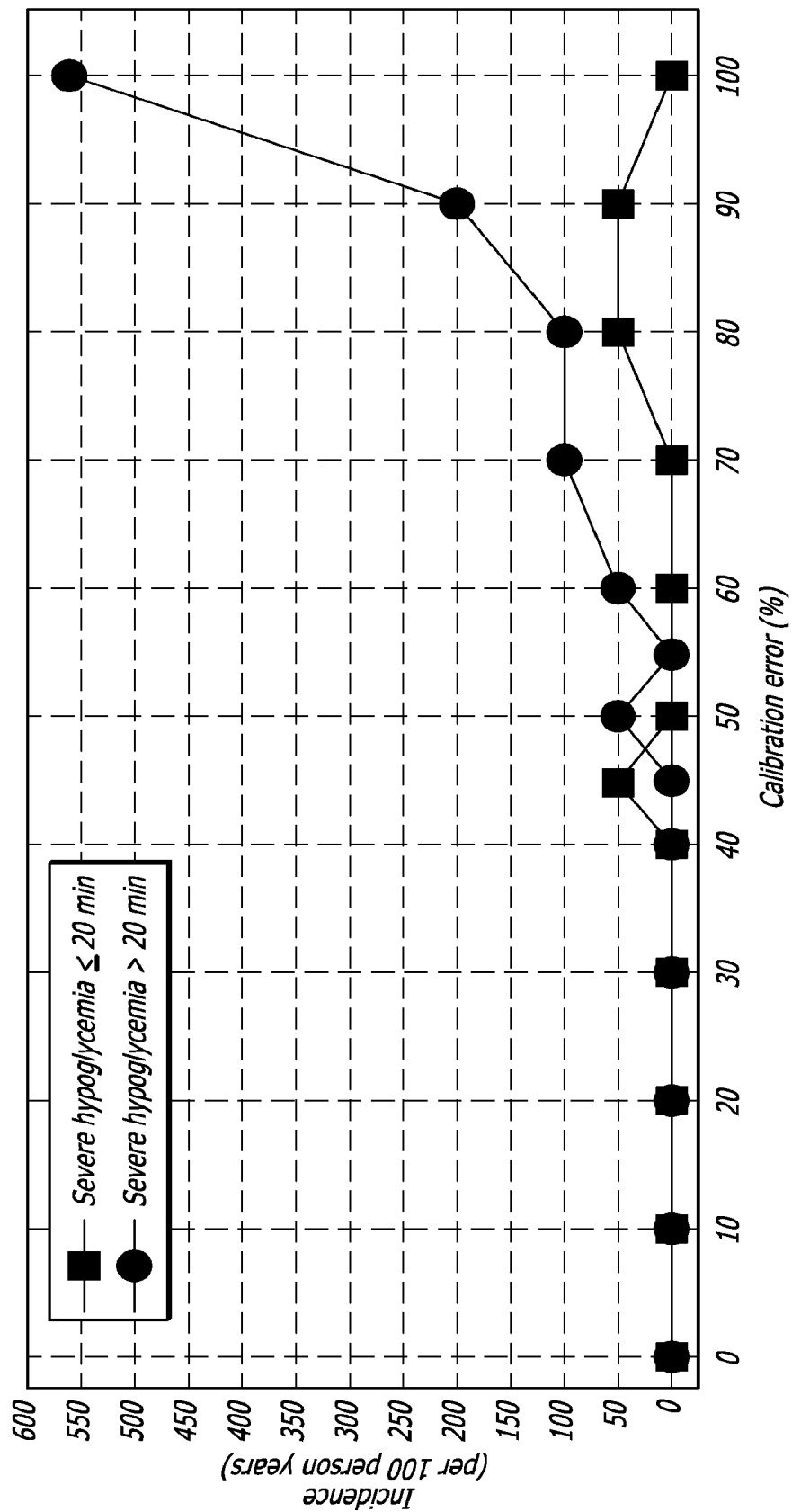
FIG. 7 presents the incidence of severe hypoglycemia (≤36 mg/dl) twenty minutes or shorter and longer than twenty minutes during simulated overnight closed-loop studies as a function of CGM system calibration error. At each level of CGM system calibration error, 720 simulations were run; the occurrence of one event in 720 simulations corresponds to around fifty events per one-hundred person years.
Figure 8:
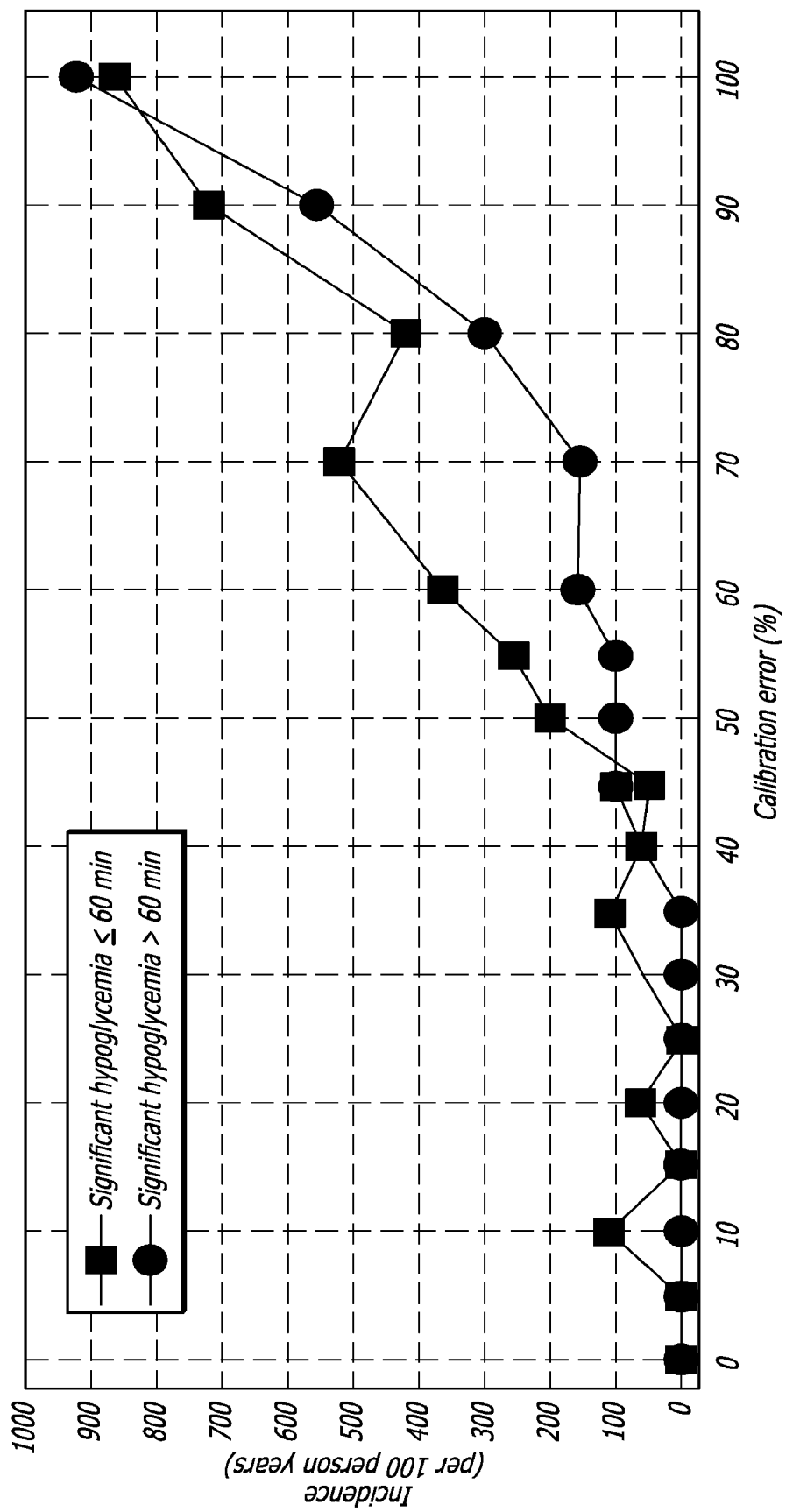
FIG. 8 presents the incidence of significant hypoglycemia (≤45 mg/dl) sixty minutes or shorter and longer than sixty minutes during simulated overnight closed-loop studies as a function of CGM system calibration error. At each level of CGM system calibration error, 720 simulations were run; the occurrence of one event in 720 simulations corresponds to around fifty events per one-hundred person years.

FIGS. 7 and 8 show the incidence of severe (PG≤36 mg/dl) and significant (PG≤45 mg/dl) hypoglycemia across FSN CE. Severe hypoglycemia did not occur at FSN CE of 40% or lower. Significant hypoglycemia did not occur at FSN CE of 5% or lower.

TABLE 2 breaks down severe hypoglycemia events according to their duration, providing more detailed information. The longest duration of severe and significant hypoglycemia occurred at the highest 100% FSN CE, lasting for 79 and 178 min, respectively.

Figure 9:
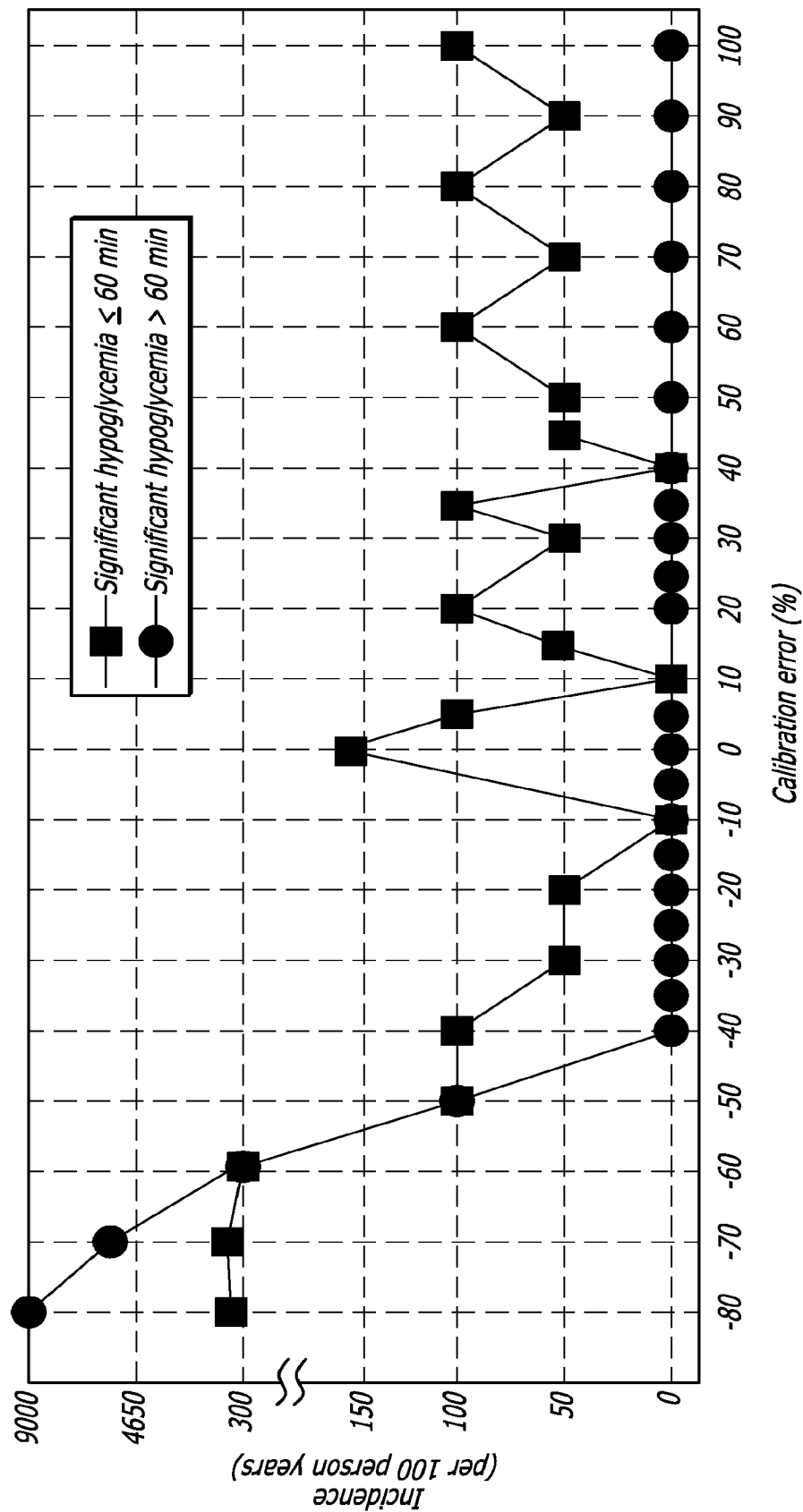
FIG. 9 plots the incidence of significant hyperglycemia (>300 mg/dl) sixty minutes or shorter and longer than sixty minutes during simulated overnight closed-loop studies as a function of CGM system calibration error. At each level of CGM system calibration error, 720 simulations were run; the occurrence of one event in 720 simulations corresponds to around fifty events per one-hundred person years.

FIG. 9 plots the incidence of significant hyperglycemia (PG≥300 mg/dl) for the different levels of FSN CE. Significant hyperglycemia lasting sixty minutes or less was present at most levels of FSN CE, while events lasting more than sixty minutes occurred when FSN CE was below −40% The longest duration of significant hyperglycemia occurred at the −80% FSN CE, lasting for 455 minutes.

FreeStyle Navigator Calibration Error Distribution

Figure 6:
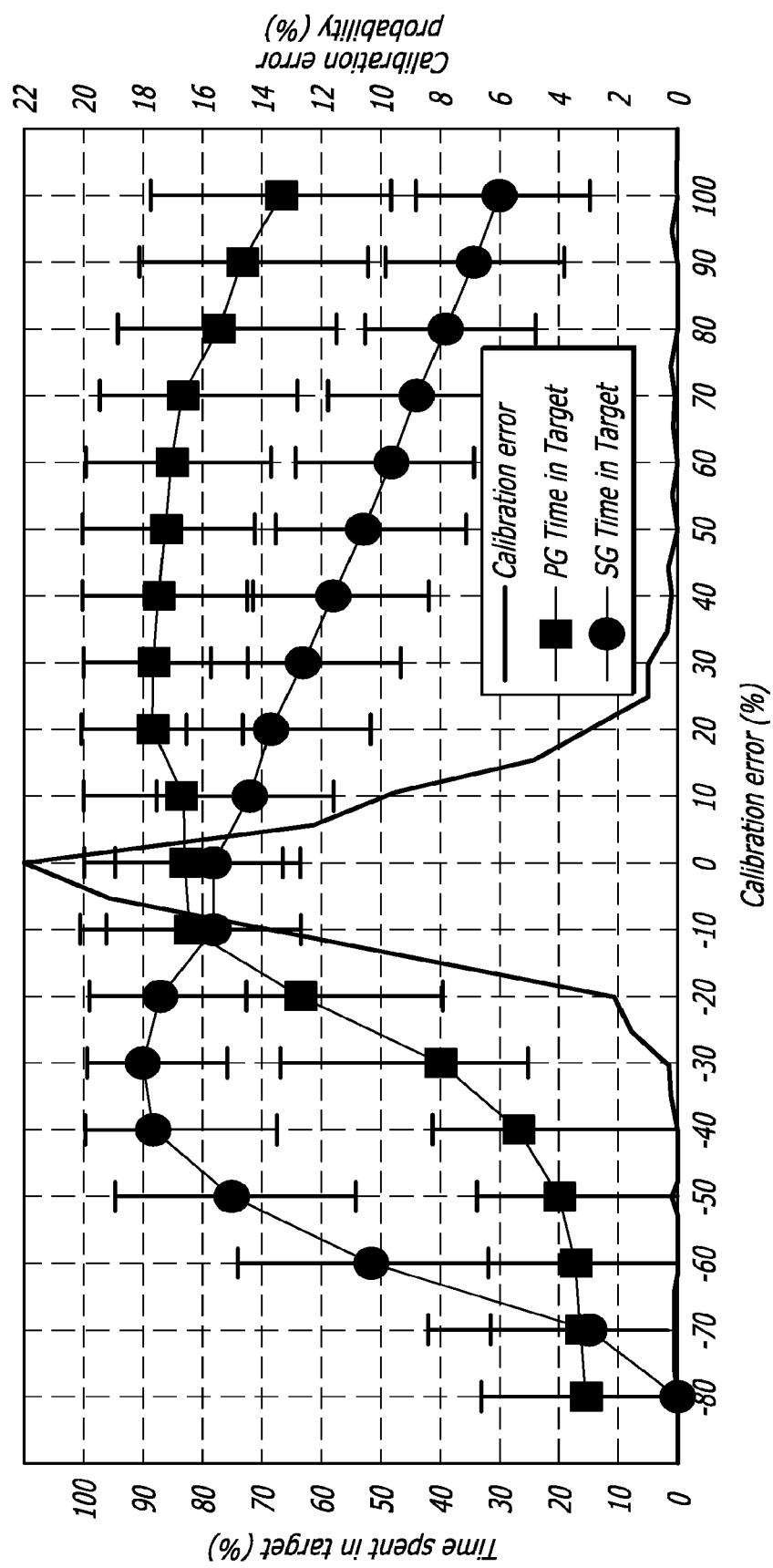
FIG. 6 is a chart showing time spent in the glucose target range (80 to 145 mg/dl) as quantified using plasma glucose and sensor glucose (medial [interquartile range]; N=720 at each level) during simulated overnight closed-loop studies at different levels of CGM system calibration error. The CGM system calibration error distribution function is also shown.

The probability distribution of FSN CE generated from 1421 calibration sessions is shown in FIG. 5 and is replicated in FIG. 6. Approximately three-fourths (¾) of the distribution resides within the −10% to +10% range of FSN CE; 35 out of 1421 (2.5% calibration sessions had FSN CE of 30% or higher. Approximately the same number of sessions (37 out of 1421) had a CE of −30% or lower. FIG. 5 presents plasma glucose and SG (median [interquartile range]; N=720 at each level) during simulated overnight closed-loop studies at different levels of FSN CE. The FSN CE probability distribution function is also shown. FIG. 6 presents time spent in the glucose target range (80 to 145 mg/dl) as quantified using PG and SG (median [interquartile range]; N=720 at each level) during simulated overnight closed-loop studies at different levels of FSN CE. The FSN CE probability distribution function is also shown.

FIG. 7 presents the incidence of severe hypoglycemia (≤36 mg/dl) 20 min or shorter and longer than 20 min during simulated overnight closed-loop studies as a function of FSN CE. At each level of FSN CE, 720 simulations were run; occurrence of one event in 720 simulations corresponds to around 50 events per 100 person years.

FIG. 8 presents the incidence of significant hypoglycemia (≤45 mg/dl) 60 min or shorter and longer than 60 min during simulated overnight closed-loop studies as a function of FSN CE. At each level of FSN CE, 720 simulations were run; occurrence of one event in 720 simulations corresponds to around 50 events per 100 person years.

Open-Loop Studies

During APCam01 and APCam03 studies, PG at 20:00 was 207±97 mg/dl. Average overnight PG from 20:00 to 08:00 was 146±65 mg/dl. Time spent in the target glucose range from 20:00 to 08:00 was 40% (18-61%) (median [interquartile range]).

During APCam03, one "severe" hypoglycemic event was observed (PG≤36 mg/dl). The subject was given Gluco-Gel®, and the study night was terminated; thus the duration of the untreated severe hypoglycemic event cannot be ascertained. Two episodes of "significant" hypoglycemia were observed (PG≤45 mg/dl): one study APCam01 over forty-five minutes in duration and another in APCam03 over seventy-five minutes in duration, preceding the severe hypoglycemic event above.

Overall Incidence of Hypoglycemia and Hyperglycemia

The overall incident of hypoglycemia and hyperglycemia during closed-loop and open-loop studies is shown in TABLE 3.

FIG. 9 presents the incidence of significant hyperglycemia (>300 mg/dl) 60 min or shorter and longer than 60 min during simulated overnight closed-loop studies as a function of FSN CE. At each level of FSN CE, 720 simulations were run; occurrence of one event in 720 simulations corresponds to around 50 events per 100 person years.

Discussion

The present study suggests that overnight closed loop combining an MPC algorithm and the FSN CGM system is expected to reduce the risk of hypoglycemia and hyperglycemia compared to the standard CSII therapy. Overnight closed-loop insulin delivery is expected to reduce the incidence of (1) severe hypoglycemia 2300-fold, (2) significant hypoglycemia 200-fold, and (3) significant hyperglycemia 200-fold.

These reductions are indicative rather than conclusive given the differences in subject populations; the lower incidence of hypoglycemia events, particularly those observed clinically during the CSII treatment; and uncertainties associated with in silico testing. It is important to stress that simulated results need to be verified with clinical data and that efforts should be made to assess true hypoglycemia incidence, which may not be indicated by SG traces alone due to the possible presence of the kinds of persistent and transient sensing errors described. In addition, as average SG levels may be reduced during closed-loop insulin delivery compared to the standard CSII treatment, the presence of transient errors due to dropouts may erroneously suggest an increase in hypoglycemic events, i.e., SG may temporarily drop below the hypoglycemic threshold while PG remains about the threshold.

The incidence calculations are influenced by three main components: 1) the persistent sensing error, 2) the transient sensing error, and 3) insulin misdosing by the control algorithm. In the present study, the assessment of the first two components is based on large observational data sets, providing solid foundations for the incidence calculations. The assessment of the last component is addressed by in silico testing. These simulations are the least strong part of our approach due to limitations of the glucose regulation model but facilitate a rational way to assess performance of a closed-loop system prior to its evaluation in larger clinical studies.

It is argued that the persistent sensing error poses a greater risk of hypoglycemia than the transient sensing error. When SG consistently exceed PG levels, the risk of undetected sustained hypoglycemia increases; for example, a 100% persistent error translates a PG reading of 50 mg/dl into a SG reading of 100 mg/dl. The persistent error reflects primarily the SG CE. The present study suggests that severe hypoglycemia arises only at an FSN CE of 45% and higher with the study-specific MPC algorithm. This represents 0.845% of the calibration segments. Thus the characterization of tails of the distribution of the SG CE is essential for the correct quantification of the hypoglycemia risk, suggesting that risk calculations can only be carried out once large data sets characterizing the performance of any particular CGM system are available.

From a closed-loop control perspective, transient errors such as dropouts could trigger a momentary reduction or cessation of insulin command due to the perceived hypoglycemia event (present or near future). Such a response might increase the risk of hyperglycemia. Closed-loop systems with a strong predictive and/or derivative term might generate a momentarily exaggerated insulin command when a rapid dropout recovery occurs. If PG is already low, then this transient response could increase the risk of hypoglycemia. The effect of dropouts is illustrated in FIG. 2. Four simulated SG traces with different levels of dropout severity are shown alongside the underlying PG measurements.

In the present study, the transient error was obtained by taking the difference of two SG traces and correcting them for CE. Methodologically, this approach overestimates the transient error as, by definition, when subtracting two SG traces, the variances of the two transient errors presented in the component SG traces add up. However, a visual inspection of simultaneously observed SG traces in quartiles two to four indicates that the transient error in one of the two SG traces typically dominates, justifying our pragmatic approach, which preserves important characteristics such as dropout clustering.

Prior investigation of the validity of the predictions made by in silico testing increases the confidence in the incidence calculations. We previously validated the virtual population of 18 subjects with T1DM by simulating a fifteen hour clinical study with an MPC algorithm.[28] The protocol of the simulated study reflected the APCam01 study conducted in twelve children and adolescents with T1DM.[20] Premeal PG during the simulated study was designed to match that of the real study (177±56 versus 171±67 mg/dl, p=not significant ("NS"); unpaired t test). Sensor glucose at the start of closed-loop control (220±72 versus 191±54 mg/dl, p=NS) and mean overnight SG (137±22 versus 141±25 mg/dl, p=NS) were similar during simulated and real studies. Time spent in the target glucose range 80 to 145 mg/dl was not significantly different at 69% (62-78%) versus 63% (49-78%) (median [interquartile range], p=NS). Kovatchev and associates' low blood glucose index [0.5 (0.2-0.9) versus 0.3 (0.0-1.0), p=NS] and high blood glucose index [3.4 (1.3-6.8) versus 3.7 (0.6-6.8), p=NS][29] were also similar during the real and simulated studies, supporting the validity of glucose predictions at low and high glucose levels.

We further assessed the validity of in silico predictions by simulating open-loop studies. First, optimum prandial and optimum basal insulin to achieve and maintain PG at 108 mg/dl were determined for the eighteen virtual subjects during a fifteen hour simulated study commencing at 17:00, with a 50 g CHO meal planned at 18:00. Then basal insulin was increased by 20% and an identical study design was simulated. Additional simulations were performed, with basal insulin increased by 55% and 85%. These increases in the basal insulin delivery corresponded to differences between the average delivered insulin rate and the average insulin rate preprogrammed on the insulin pump during thirty-three overnight closed-loop studies in young people with T1DM treated by CSII.[30] In these thirty-three closed-loop studies, a 20% overestimation of basal insulin was observed in three studies, a 55% overestimation in four studies, and an 85% overestimation in one study.

At the 20% overestimation of basal insulin, the simulations yielded no severe hypoglycemia and one significant hypoglycemia in the eighteen virtual subjects. At the 55% overestimation, five and three hypoglycemia events were observed. At the 85% overestimation, eight and two events occurred. This indicates the incidence of severe hypoglycemia during simulated studies at 1720 per 100 person years, which tallies extremely well with a corresponding incidence of 1739 per 100 person years recorded during "true" open loop studies (see Table 3). The incidence of significant hypoglycemia during simulations was 1044 per 100 person years, which is less but still comparable to that observed experimentally at 3479 per 100 person years; the difference in the incidence rates corresponds to two significant hypoglycemia events over thirty-three nights. Overall, these results suggest that in silico simulations provide acceptable predictions of hypoglycemia incidence during open-loop studies, supporting the validity of in silico predictions during closed-loop studies.

The MPC algorithm used in the present study has important in-built safety features. It uses the pre-programmed insulin infusion rate as an initial estimate of the insulin needed to achieve normoglycemia. If SG increases, the MPC algorithm controller steps up insulin delivery but does so cautiously and at the expense of suboptimal SG levels. This is evident in FIGS. 5 and 6, which demonstrate that, with increasing levels of FSN CE, the mean SG concentration increases and the time-in-target assessed with the use of SG decreases. This design feature of the MPC algorithm reduces the impact of FSN CE on the risk of hypoglycemia.

Figure 10:
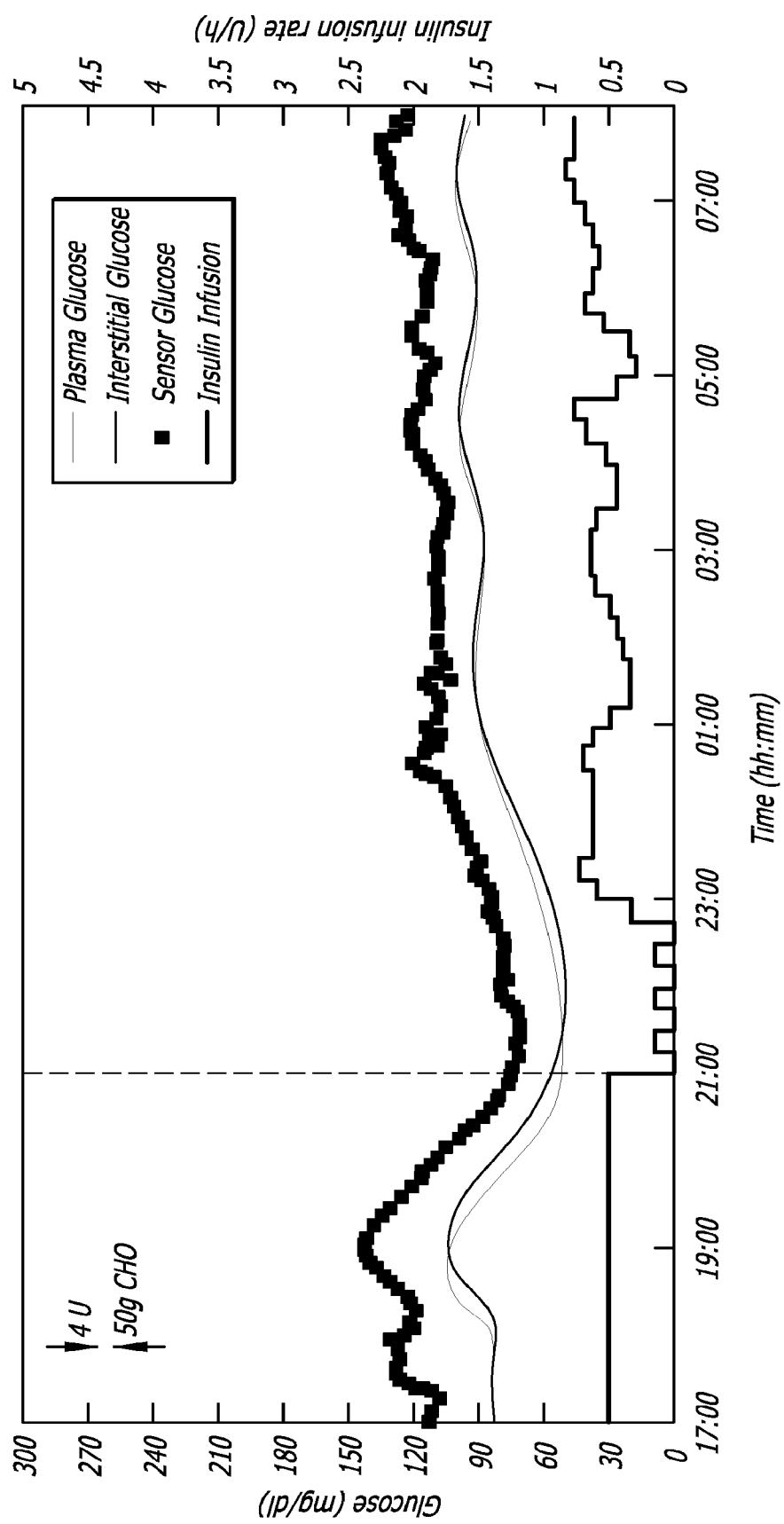
FIG. 10 provides a sample simulation showing hypoglycemia due to prandial insulin overdosing.

The simulation study design included a relatively small evening meal compared to the body weight of the virtual subjects. Additionally, pre-meal PG was constrained to levels between 72 and 180 mg/dl. In combination, these two study design aspects limit postprandial hyperglycemia excursions, which are expected to be more pronounced after larger meal sizes and at elevated premeal PG values. Conversely, prandial insulin overdosing due to overestimation of the meal size may result in early postprandial hypoglycemia, which cannot be prevented by closed-loop insulin delivery even if insulin infusion is stopped. Some of the episodes of hypoglycemia observed in the present study were directly attributable to prandial insulin overdosing prior to the start of closed-loop control. An example is shown in FIG. 10, where the insulin overdelivery is confounded by a ±30% FSN CE. Hypoglycemia occurred prior to the start of the closed-loop session. Although insulin delivery virtually stopped at the start of closed loop, PG and SG continued to decrease for another thirty minutes. The hypoglycemia event remained undetected, as SG did not reach the hypoglycemia threshold of 63 mg/dl.

The use of CGM alone is expected to reduce the hypoglycemia and hyperglycemia risks as observed in the *Juvenile Diabetes Research Foundation* CGM trial.[31] The observed improvements are clinically important but lack the scale offered by the overnight closed-loop approach. However, even the overnight closed-loop approach, the risk of hypoglycemia and hyperglycemia is not eliminated. The duration of significant and severe hypoglycemia during simulation studies is limited to one and three hours, which is slightly less than the two to four hours of SG-documented hypoglycemia that has been reported prior to seizures.

FIG. 10 presents a sample simulation showing hypoglycemia due to prandial insulin overdosing. Prandial insulin accompanied the meal at 18:00. The closed loop started at 21:00. Sensor glucose was obtained using a +30% FSN CE and a dropout trace from quartile two. Hypoglycemia occurred before the start of the closed-loop session and continued to worsen for another thirty minutes after the start of closed loop although insulin delivery was virtually turned off. Hypoglycemia was undetected, as SG did not reach the hypoglycemia threshold of 63 mg/dl. FreeStyle Navigator CE at +30% or higher is estimated to occur 2.5% of the time, assuming no recalibration is performed between scheduled calibrations.

The FSN CE distribution shown in FIGS. 5 and 6 was constructed assuming that only the five FSN scheduled calibrations are performed. If a manual recalibration was performed to rectify excessive CEs that would have been evident when SG was compared against a finger stick reading, the risk of hypoglycemia and hyperglycemia during overnight closed loop could be further reduced.

More detailed information about transient and persistent sensing errors is required to determine if the present results may be transferable to other commercially available CGM systems.[33] Transferability to other control algorithms is uncertain given the wide range of control approaches.

In conclusion, overnight closed loop using an MPC algorithm and real-time glucose sensing by the FSN system may offer a 200-2300-fold reduction of the hypoglycemia and hyperglycemia incidence. This suggests that existing continuous glucose sensing technologies facilitate safe closed-loop insulin delivery, although confirmation in large clinical studies is required.

ABBREVIATION LIST

| Abbrev. | Stands for: |
|---|---|
| A1C | hemoglobin A1C |
| APCam | Artificial Pancreas Cambridge |
| BMI | body mass index |
| CE | calibration error of FreeStyle Navigator System |
| CGM | continuous glucose monitoring |
| CHO | carbohydrate |
| CL | closed loop |
| CSII | continuous subcutaneous insulin infusion |
| dl | deciliter |
| D(t) | dropout trace of FreeStyle Navigator System |
| FSN | FreeStyle Navigator Continuous Glucose Monitoring System |
| g | grams |
| IG | interstitial glucose |
| l | liter |
| mg/dl | milligrams per deciliter |
| MPC | model predictive control |
| NS | not significant |
| OL | open loop |
| PG | plasma glucose |
| SC | subcutaneous glucose concentration |
| SD | standard deviation |
| SG | sensor glucose |
| T1DM | type 1 diabetes mellitus |
| T2DM | type 2 diabetes mellitus |
| $VO_2$ | Maximal oxygen uptake, which is accepted as a measure of cardiovascular fitness and maximal aerobic power. Also referred to as maximal oxygen consumption, maximal oxygen uptake, or aerobic capacity. |

Table 4 includes a list of documents to which reference is made by means of endnotes in the text above. Each of those documents listed in Table 4 is hereby incorporated by reference.

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims.

The invention claimed is:

1. A system for a delivery of insulin to a patient, the system comprising:
a glucose sensor configured to provide a sensor glucose measurement signal representative of sensed glucose;
an insulin delivery device configured to deliver insulin to a patient in response to control signals; and
a controller programmed to receive the sensor glucose measurement signal and to provide a delivery control signal to the insulin delivery device as a function of the sensor glucose measurement signal received by the controller in accordance with a model predictive control and a glucose measurement error model, the glucose measurement error model derived from actual glucose sensor measurement data,
wherein the delivery control signal is adjusted based at least in part on sensor error.

2. The system of claim 1, wherein the sensor error is one or more of sensor dropout and calibration error.

3. The system of claim 1, wherein the delivery control signal is adjusted based at least in part on the sensor error to reduce a risk of hypoglycemia.

4. The system of claim 1, wherein the delivery control signal adjusted based at least in part on the sensor error includes using a pre-programmed insulin infusion rate as an initial estimate of insulin to reduce a risk of hypoglycemia due to the sensor error.

5. The system of claim 1, wherein the model predictive control is based on a glucoregulatory model.

6. The system of claim 1, wherein the delivery control signal adjusted based at least in part on the sensor error is further adjusted based on one or more of a weight of the patient, a total daily insulin dose of the patient, and a basal insulin profile of the patient.

7. The system of claim 1, wherein the controller is further programmed to adjust a value of the delivery control signal based at least in part on the sensor error in accordance with a forecasted future plasma glucose level excursion.

8. The system of claim 1, wherein the controller is further programmed to adjust a value of the delivery control signal based at least in part on the sensor error in accordance with a safety check.

9. The system of claim 8, wherein the safety check is one or more of imposing a maximum infusion rate related to a basal rate, shutting off insulin delivery at a predetermined low sensed glucose value, reducing insulin delivery when the sensed glucose is decreasing rapidly, and capping insulin delivery to a pre-programmed basal rate if occlusion of the insulin delivery device is inferred.

10. The system of claim 1, wherein the actual glucose sensor measurement data excludes one or more of sensor noise data and randomly generated variable data.

11. A method for delivering insulin to a patient, the method comprising:
sensing a glucose level with a glucose sensor and providing a sensed glucose measurement signal;
providing a delivery control signal as a function of the sensed glucose measurement signal in accordance with a model predictive control and a glucose measurement error model, the glucose measurement error model derived from actual glucose sensor measurement data, wherein the delivery control signal is adjusted based at least in part on sensor error; and delivering insulin in response to the delivery control signal.

12. The method of claim 11, wherein the sensor error is one or more of sensor dropout and calibration error.

13. The method of claim 11, wherein the delivery control signal is adjusted based at least in part on the sensor error to reduce a risk of hypoglycemia.

14. The method of claim 11, wherein providing the delivery control signal adjusted based at least in part on the sensor error further comprises using a pre-programmed insulin infusion rate as an initial estimate of insulin to reduce a risk of hypoglycemia due to the sensor error.

15. The method of claim 11, wherein the model predictive control is based on a glucoregulatory model.

16. The method of claim 11, wherein providing the delivery control signal adjusted based at least in part on the sensor error further comprises adjusting the delivery control signal based on one or more of a weight of the patient, a total daily insulin dose of the patient, and a basal insulin profile of the patient.

17. The method of claim 11, further comprising adjusting a value of the delivery control signal based at least in part on the sensor error in accordance with a forecasted future plasma glucose level excursion.

18. The method of claim 11, further comprising adjusting a value of the delivery control signal based at least in part on the sensor error in accordance with a safety check.

19. The method of claim 18, wherein the safety check is one or more of imposing a maximum infusion rate related to a basal rate, shutting off insulin delivery at a predetermined low sensed glucose value, reducing insulin delivery when the sensed glucose is decreasing rapidly, and capping insulin delivery to a pre-programmed basal rate if occlusion of the insulin delivery device is inferred.

20. The method of claim 11, wherein the actual glucose sensor measurement data excludes one or more of sensor noise data and randomly generated variable data.

* * * * *